United States Patent [19]

Figura

[11] 3,942,052
[45] Mar. 2, 1976

[54] TORSION VIBRATOR OF A SUPERSONIC VISCOSIMETER

[75] Inventor: Zdeno Figura, Bosaca, Czechoslovakia

[73] Assignee: Vyskumny ustav mechanizacia a automatizacie, Nove Mesto nad Vahom, Czechoslovakia

[22] Filed: Sept. 11, 1974

[21] Appl. No.: 505,060

Related U.S. Application Data

[63] Continuation-in-part of Ser. No. 340,331, March 12, 1973, abandoned.

[30] Foreign Application Priority Data

July 19, 1972 Czechoslovakia .................. 5107-72

[52] U.S. Cl. ........................................ 310/26; 73/59
[51] Int. Cl.² ........................................ H01L 41/12
[58] Field of Search ............ 73/59; 310/26; 318/118

[56] References Cited
UNITED STATES PATENTS

| 2,701,469 | 2/1955 | Burns, Jr. | 73/59 |
| 2,839,915 | 6/1958 | Roth et al. | 73/59 |
| 3,419,825 | 12/1968 | La Manna | 310/26 X |

FOREIGN PATENTS OR APPLICATIONS

| 830,463 | 3/1960 | United Kingdom | 310/26 |

*Primary Examiner*—Donovan F. Duggan

[57] ABSTRACT

A torsion vibrator for a supersonic viscosimeter having a magnetostrictive bar fixed at both ends to the case of the vibrator and passing through a toroidal transformer. A lower resonator is mechanically connected to the lower end of the magnetostrictive bar and an upper resonator, passing through a pick-up coil, is connected to the upper end of the magnetostrictive bar.

5 Claims, 1 Drawing Figure

U.S. Patent  March 2, 1976  3,942,052
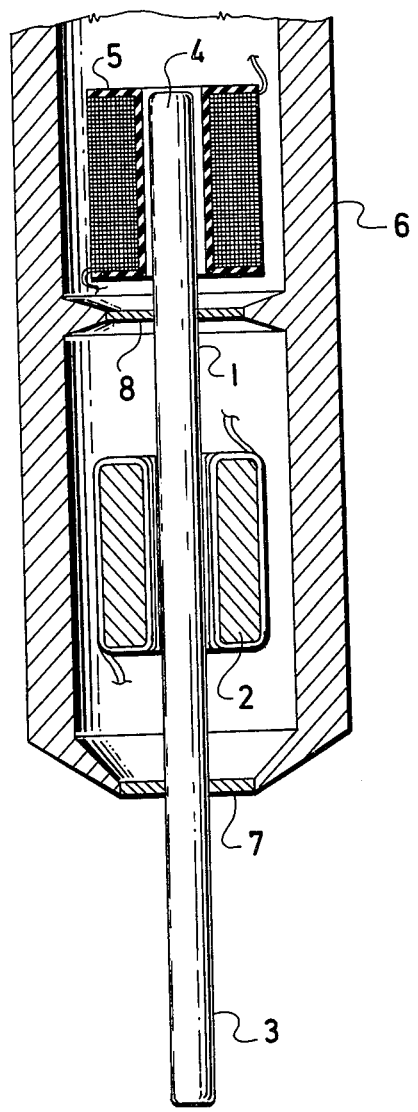

3,942,052

TORSION VIBRATOR OF A SUPERSONIC VISCOSIMETER

RELATED IN APPLICATION

The present application is a continuation in part of applicant's co-pending application, Ser. No. 340,331, filed Mar. 12, 1973, now abandoned, the disclosure of which is incorporated herein as if more fully set forth.

BACKGROUND OF THE INVENTION

The present invention relates to a vibrator for a viscosimeter having a resonator fixed at two spaced points within a casing. One end of the resonator is adapted to extend from the casing to make contact with the liquid while the other end is surrounded by a pick-up coil adapted to set the oscillation of the resonator. The central part of the resonator comprises an exciting magnetostrictive bar.

Known supersonic torsion resonators or vibrators of this type, are used for continuous measurement of the viscosity of the liquid and consist of a half-wave resonator, fixed at its center so that one free end is in contact with the liquid to be measured. The other end serves for excitation and for picking up the oscillation of the resonator. Another known device, uses a torsion resonator, the length of which is equal to a half-wave or a multiple of a half-wave of the torsion oscillations in the respective material being measured. The resonator of this latter device is fixed at one nodal point and excited by a tangentially fixed supersonic logitudinally oscillating transducer in the oscillation node. A pick-up transducer is also tangentially fixed and stacked about 180° with respect to the exicting transducer. These devices have the drawback that the tuning of both halves of the resonator, the Q of which is very high, is rather troublesome.

Other methods, which have attempted to eliminate these drawbacks present a great deal of difficulty in their construction and in their connection, particularly when applied in explosive or chemically aggressive and dangerous media. Such attempts to eliminate the drawback have used, for instance, the excitation simultaneously of both halves of the resonator.

Another drawback of the known devices is the limited mechanical resistivity of the construction, particularly for the measurements of flowing liquids the stream of which is not exactly laminar or linear. The influence of the electric or magnetic field of the exciting pulse, created by the flowing liquid, on the picked up electrical signal acts disturbingly in the measurement circuit.

Still further, in torsionally oscillating resignators, wherein magnetostriction phenomena is used for exciting torsional oscillations and wherein scanning is carried out on the basis of Weidemann's phenomenon in case of fixation at one nodal point of resonator oscillations, the amplitude/frequency is represented by two expressive maxima corresponding to the first harmonic of resonant frequencies of both the torsional and longitudinal wave, excited by the resonator. Therefore, it is impossible to achieve an electrical evaluation, by means of a pulsing excitation of the resonator, since on the scanning coil there are obtained voltages corresponding to both the longitudinal and torsional free oscillations of the resonator.

It is, therefore, the object of the present invention to reduce the drawbacks, enumerated above, in the use of the known torsion resonators and vibrators, and to produce a torsion vibrator for a supersonic viscosimeter which is simple in construction and use and which is highly effective.

SUMMARY OF THE INVENTION

According to the present invention, a torsion vibrator for a supersonic viscosimeter is provided having a casing in which is located a toroidal transformer and an electrically conductive magnetostrictive bar extending through the transformer. The magnetostrictive bar is connected at its upper and lower ends, respectively, by a coupling to the casing. A magnetostrictive resonator is mechanically connected to the lower end of the magnetostrictive bar and extends freely from the case. An upper magnetostrictive resonator is connected to the upper end of the magnetostrictive bar and extending through the case as well. A pick-up coil is located within the case and surrounds the upper magnetostrictive resonator. The magnetostrictive bar, the upper and lower couplings, and the case, combine to form the secondary winding of the toroidal transformer, which is otherwise without a normal coil.

Preferably the length of the magnetostrictive bar is equal to one-half of the wavelength of the material while the length of the lower resonator is preferably an uneven multiple of one-quarter of the wavelength of the material used. The material of the lower resonator is different from the material of the magnetostrictive bar and as well is different from the material used in the upper magnetostrictive resonator.

By arrangement of the supersonic torsion resonators according to the present invention a number of advantages are achieved in the vibrator as a whole. Namely: a mutual separation of the exciting and pick-up part is effected and their perfect screening is obtained; the fixing at two nodal points thus improves mechanical resistivity and provides a reduction of the difficulties in tuning of the vibrator. An advantage is also obtained in that the electrically conductive magnetostrictive bar together with the electrically conductive couplings constitute a secondary winding of the exciting transformer. This results in a simpler and less expensive vibrator construction, together with substantially higher mechanical strength and sturdiness of the resonator probe extending from the casing, as compared with the known strip-shaped and tubular resonators. One of the merits of the present invention lies in a damped longitudinal component of the resonator oscillations so that the vibrator can be excited by discrete separate impulses and the damping of the free torsional resonator oscillations can be evaluated.

Full details of the present invention follow herein and are shown in the accompanying drawing.

BRIEF DESCRIPTION OF THE DRAWING

An exemplary embodiment of the torsion vibrator for a supersonic viscosimeter, embodying the present invention, is shown in the longitudinal cross-sectional elevation of the FIGURE.

DESCRIPTION OF THE INVENTION

The torsion vibrator comprises a magnetostrictive bar 1, around which the primary winding of a toroidal exciting transformer 2 is located. Connected mechanically to the lower end of the magnetostrictive bar 1 is a quarter-wave resonator 3 while connected to the upper end of the magnetostrictive bar 1 is a quarter-wave resonator 4. A pick-up coil 5 surrounds the upper quarter-wave resonator 4 and a casing surrounds the entire assembly, allowing the lower resonator 3 to extend outwardly from it. Electrically conductive couplings 7 and 8 located respectively at the lower and upper ends of the magnetostrictive bar 1, connect the bar to the outer casing. The magnetostrictive bar 1 is of course electrically conductive, the lower quarter-wave resonator 3 is made of material different from the bar. The upper quarter-wave resonator 4 is made of material different from that of the lower resonator 3 and may also be made magnetostrictive.

The material from which an electrically conductive magnetostrictive bar can be formed is well known to those skilled in the present art. Reference can be made to Kikuchi, Y. "Ultrasonic Transducers", published by the Corona Publishing Co. Ltd. of Tokyo, 1969, particularly p. 96, Table 4.2, or Hueter, T. P. and Bolt, R. H., "Sonics," published by John Wiley & Sons, Inc., 1955, particularly on p. 175 Table 5.1.

The torsion resonator is arranged in such a manner that the electrically conductive magnetostrictive bar 1 has a length equal to the upper half of the wavelength of the torsional oscillations thereof. The length of the lower resonator 3 is an uneven multiple of the length of the torsion wave of the material used and preferably is one-fourth of the wavelength. The connections between the magnetostrictive bar and the resonators 3 and 4 are conventional, care being taken that they are connected axially and fixedly so as not to be separable.

It will be seen from the foregoing that the toroidal transformer is provided with only its primary coil. The electrically conductive magnetostrictive bar 1 and the electrically conductive couplings 7 and 8 together with the casing 6, which is also conductive, combine to form the secondary winding for the toroidal transformer. As a result the advantages in simplicity of construction and function as well as its accuracy in both supersonic and ultrasonic measurements is obtained.

The torsion vibrator operates as follows.

A unidirectional or high frequency current impulse passing through the primary coil or winding of the exciting transformer 2 generates an electric current in the secondary coil formed by the magnetostrictive bar 1, the electrically conductive couplings 7 and 8 and the casing 6. This generated current creates a concentrated magnet field in the magnetostrictive bar 1 itself. Due to the magnetostrictive effect, the bar 1, responsive to a unidirectional impulse, is shifted at a predefined angle, or, responsive to a high frequency impulse, starts oscillating in the rhythm of an alternating excitation. When the exciting impulse ends or is finished, the resonator will continue to oscillate with an amplitude determined by the damping decrement $\alpha$ of the mechanical resonance system. This decrement will depend upon the properties of the measured Newton liquid according to the known formula:

$$\alpha = K \sqrt{\eta \phi}$$

where
 $K$ is a constant
 $\eta$ is the viscosity of the liquid
 $\phi$ is the mass of the liquid, surrounding the lower quarter-wave resonator 3.

Due to the Wiedmann effect, a voltage proportional to the amplitude of the oscillations of the resonator 4 is generated in the pick-up coil 5 which is then sent and employed, as is well known in this art.

It will be seen from the foregoing that the various objects and advantages of the present invention, enumerated earlier, have been carried out into practice. It is intended that the present disclosure be taken as illustrative only and not as limiting of the present invention.

What is claimed is:

1. A torsion vibrator for a supersonic viscosimeter comprising in combination a case, an electrically conductive magnetostrictive bar having an upper and a lower end, a toroidal transformer for exciting said magnetostrictive bar, said magnetostrictive bar being connected with the case at its upper end by an upper coupling and at its lower end by a lower coupling, and passing through said toroidal transformer, a lower magnetostrictive resonator mechanically connected to the lower end of the magnetostrictive bar and extending freely from said case, an upper magnetostrictive resonator connected to the upper end of the magnetostrictive bar extending through said case, said magnetostrictive bar, said upper and lower couplings and said case combining to form the secondary winding of said toroidal transformer, and a pick-up coil located within said case and surrounding the upper magnetostrictive resonator.

2. The torsion vibrator according to claim 1 wherein said toroidal transformer comprises a primary winding only.

3. A torsion vibrator according to claim 1 wherein the length of the electrically conductive magnetostrictive bar equals half of the wavelength of the torsional oscillations of said bar.

4. The torsion vibrator according to claim 1 wherein the length of the lower resonator is an uneven multiple of the length of the wavelength of the material used.

5. The torsion vibrator according to claim 1 wherein the material of the lower resonator is different from the material of the magnetostrictive bar and of the upper magnetostrictive resonator.

* * * * *